United States Patent [19]
Shiery et al.

[11] Patent Number: 5,924,658
[45] Date of Patent: Jul. 20, 1999

[54] IV POLE

[75] Inventors: Jeffrey C. Shiery, East Leroy; Stanley T. Palmatier, Paw Paw, both of Mich.

[73] Assignee: Stryker Corporation, Kalamazoo, Mich.

[21] Appl. No.: 09/003,776

[22] Filed: Jan. 7, 1998

[51] Int. Cl.⁶ ........................................... A47F 5/00
[52] U.S. Cl. .................. 248/125.8; 248/161; 248/188.5; 403/109.1
[58] Field of Search .................. 248/125.8, 161, 248/354.1, 354.5, 411, 529; 403/109.1, 376; 411/265; 297/344.18

[56] References Cited

U.S. PATENT DOCUMENTS

| | | | |
|---|---|---|---|
| 1,988,037 | 1/1935 | Fuerrer | 155/94 |
| 2,461,915 | 2/1949 | Neuwirth | 248/188.5 |
| 3,991,964 | 11/1976 | Christopher | 248/354.1 |
| 4,037,839 | 7/1977 | Nelson | 273/84 |
| 4,640,484 | 2/1987 | Lamond et al. | 248/407 |
| 4,684,098 | 8/1987 | Lamond et al. | 248/407 |
| 5,011,174 | 4/1991 | Ross-Clunis | 248/161 |
| 5,069,570 | 12/1991 | Pryor et al. | 403/109 |
| 5,078,349 | 1/1992 | Smith | 248/125 |
| 5,593,239 | 1/1997 | Sallee | 403/109 |

Primary Examiner—Leslie A. Braun
Assistant Examiner—Robert Lipcsik
Attorney, Agent, or Firm—Flynn, Thiel, Boutell & Tanis, P.C.

[57] ABSTRACT

A telescoping IV pole has a bottom pole with a support at a bottom end thereof for facilitating an orienting of said bottom pole in an upright, vertically oriented position. A top pole is provided which is slidably disposed within the bottom pole in a telescoping manner. The top pole has at a top end thereof an intravenous fluid container support and at a bottom end thereof a circumferential locking groove. A pole latch is provided for automatically effecting an interlock with the locking groove when the top pole is deployed to an extended position outside of the bottom pole. The pole latch includes plural latch members each being supported for movement into and out of the locking groove. A spring is provided for urging the latch members into the locking groove. A manually operable unlocking device is provided for effecting a simultaneous release of the interlock so that the top pole will telescope into the bottom pole. A control device is provided for effecting simultaneous rotational and axial translational movement of the manually operable unlocking device relative to the top and bottom poles so as to effect a simultaneous forceful urging of the latch members of the locking groove against the urging of the spring.

15 Claims, 2 Drawing Sheets

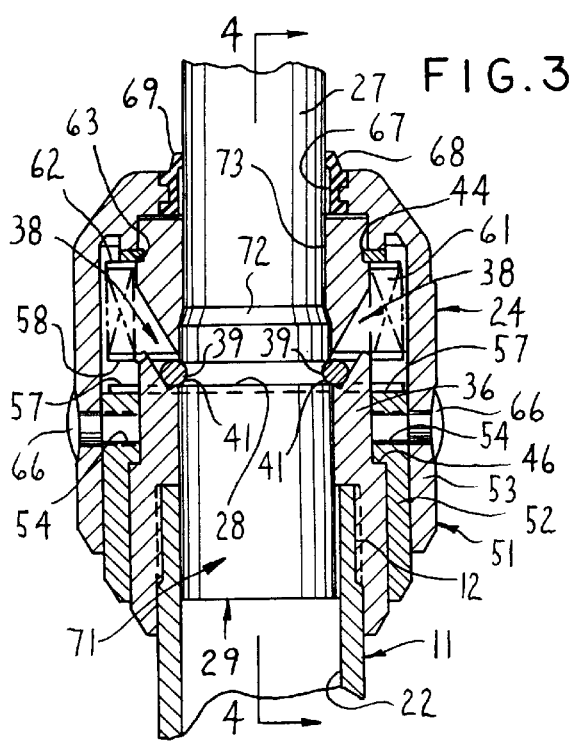
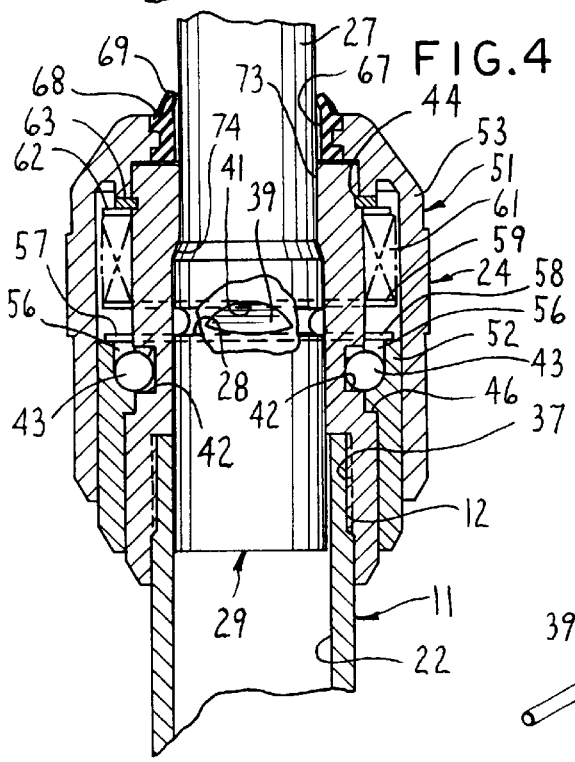
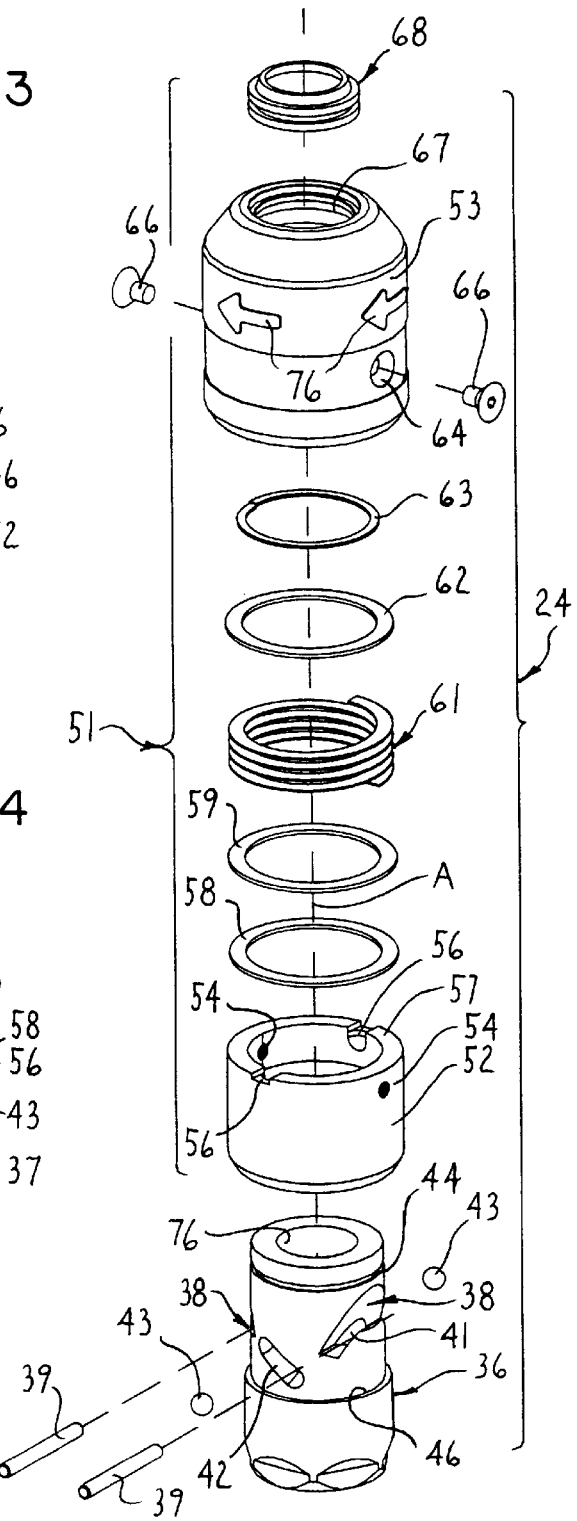

IV POLE

FIELD OF THE INVENTION

This invention relates to an IV pole latch and, more particularly, to an IV pole latch that automatically latches when the top pole is deployed to its fully extended length relative to the bottom pole.

BACKGROUND OF THE INVENTION

Many varieties of IV poles exist in the field and for the purpose of supporting intravenous fluid containers to facilitate the gravity feed of fluids contained therein to patients oriented in an adjacent bed. In many instances, the IV pole is provided on a wheeled carriage which stands adjacent the bed. In some instances, the IV pole is to be mounted directly on the bed and, in this instance, it is desired to frequently raise and lower the IV pole during periods of use and non-use. Accordingly, it is a desire to provide an IV pole with a latch mechanism that will reliably latch to the top pole when it is moved to the fully extended position thereof and to reliably release the latching engagement to facilitate a retraction of the top pole into the bottom pole. It is furthermore a desire to provide an IV pole that is sturdy once it is moved to the raised position.

Accordingly, it is an object of the invention to provide an IV pole with a latch that automatically couples to the top pole when it is moved to the fully extended position thereof.

It is a further object of the invention to provide an IV pole, as aforesaid, wherein the latch can be reliably unlocked from its engagement with the top pole to facilitate a retraction of the top pole into the bottom pole.

It is a further object of the invention to provide an IV pole, as aforesaid, which includes structure for orienting and reliably maintaining the IV pole in an upright fixed position relative to the base upon which it is mounted.

It is a further object of the invention to provide an IV pole, as aforesaid, which is reliable, requires little or no maintenance and is easy to operate by the personnel attending a patient.

SUMMARY OF THE INVENTION

The objects and purposes of this invention have been met by providing a telescoping IV pole having a bottom pole with a support at a bottom end thereof for facilitating an orienting of said bottom pole in an upright, vertically oriented position. A top pole is provided which is slidably disposed within the bottom pole in a telescoping manner. The top pole has at a top end thereof an intravenous fluid container support and at a bottom end thereof a circumferential locking groove. A pole latch is provided for automatically effecting an interlock with the locking groove when the top pole is deployed to an extended position outside of the bottom pole. The pole latch includes plural latch members each being supported for movement into and out of the locking groove. A spring is provided for urging the latch members into the locking groove. A manually operable unlocking device is provided for effecting a simultaneous release of the interlock so that the top pole will telescope into the bottom pole. A control device is provided for effecting simultaneous rotational and axial translational movement of the manually operable unlocking device relative to the top and bottom poles so as to effect a simultaneous forceful urging of the latch members of the locking groove against the urging of the spring.

BRIEF DESCRIPTION OF THE DRAWINGS

Other objects and purposes of this invention will be apparent to persons acquainted with apparatus of this general type upon reading the following specification and inspecting the following drawings, in which:

FIG. 2 is an exploded isometric view of a latch mechanism embodying the invention;

FIG. 3 is a longitudinal central sectional view of an assembly of the latch illustrated in FIG. 2; and FIG. 4 is a sectional view taken along the line 4—4 of FIG. 3.

DETAILED DESCRIPTION

Figure 1:
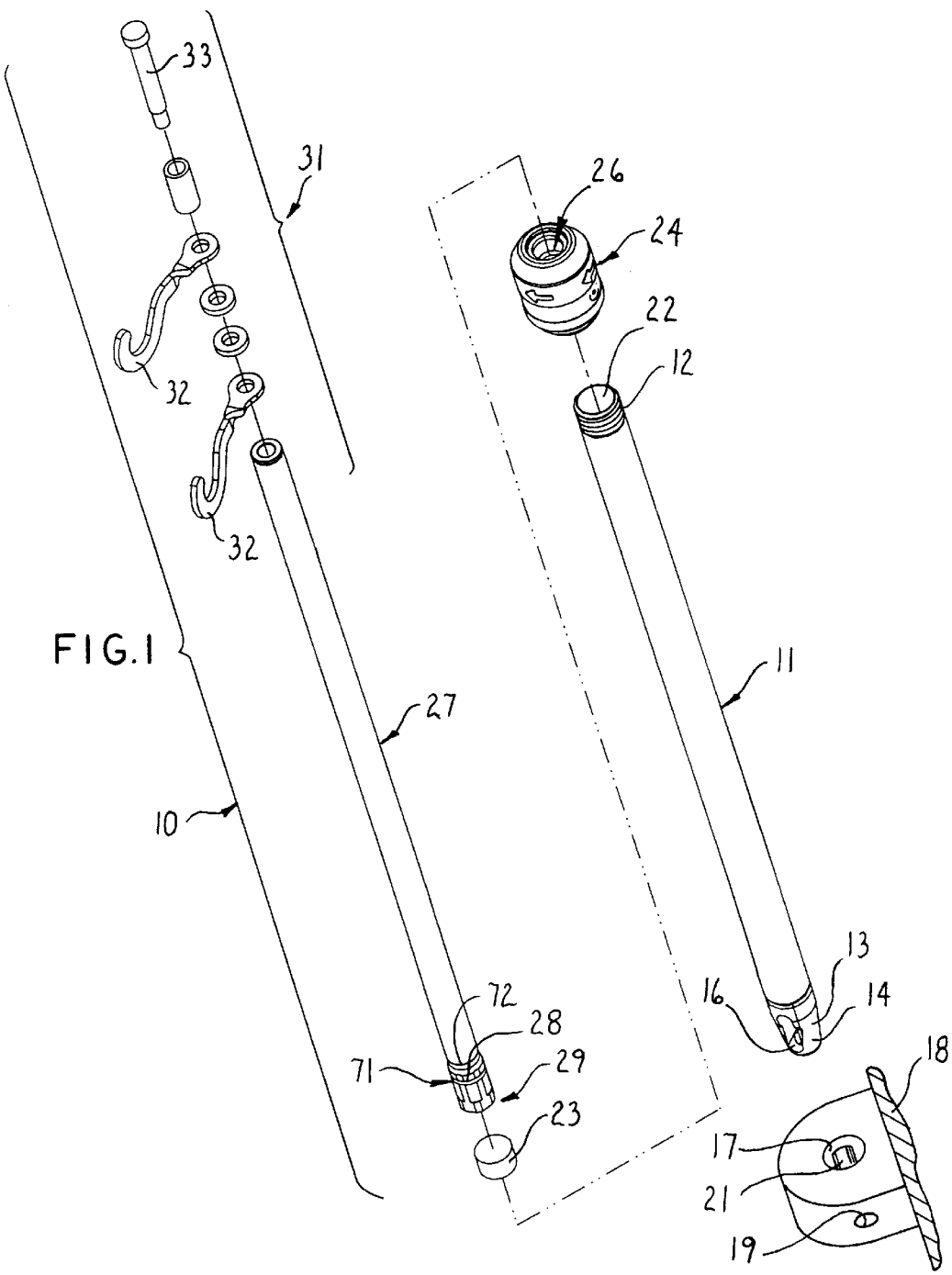
FIG. 1 is an exploded isometric view of an IV pole embodying the invention.

Certain terminology will be used in the following description for convenience and reference only and will not be limiting. The words "up", "down", "right" and "left" will designate direction in the drawings to which reference is made. The words "in" and "out" will refer to directions toward and away from, respectively, the geometric center of the device and designated parts thereof. Such terminology will include derivatives and words of similar import.

An IV pole 10 embodying the invention is illustrated in FIG. 1. The IV pole 10 includes a bottom pole 11 having an external thread 12 at an upper end thereof and a tapered fitting 13 at the lower end thereof. The exterior surface 14 of the tapered fitting 13 is preferably conical and has a transversely extending hole 16 therethrough. The tapered fitting 13 is adapted to be received into a correspondingly tapered recess 17 in a base member 18. If desired, a hole 19 can be provided in the portion of the base 18 containing the recess 17, the axis of which hole intersects the axis of the recess 17 so that a pin 21 can be received in the hole 19 and the hole 16 aligned therewith when the tapered fitting 13 is received into the recess 17. The corresponding tapered surfaces of the tapered fitting 13 and the tapered recess 17 cause a zero tolerance fitting of the tapered fitting 13 into the recess 17. As a result, the bottom pole 11 will be retained in a sturdy upright position when the tapered fitting 13 is appropriately received in the recess 17.

In this particular embodiment, the bottom pole 11 has a hollow interior 22 into which is received a cylinder shaped elastically yieldable cushion member 23. The cushion member 23 is oriented adjacent the tapered fitting 13 adjacent the bottom end of the bottom pole 11.

A pole latching mechanism 24 is threadedly secured to the thread 12 on the upper end of the bottom pole 11. The latching mechanism 24 will be described in more detail below. The latching mechanism 24 has a central passageway 26 therethrough.

A top pole 27 is telescopically received into the interior 22 of the bottom pole 11. The top pole also extends through the passageway 26 in the latching mechanism 24. The top pole includes a locking groove 28 adjacent the lower end 29 thereof.

An intravenous fluid container support mechanism 31 is secured to the upper end of the top pole 27. In this particular embodiment, the support mechanism 31 includes a pair of hooks 32. The hooks 32 have an eyelet with a central opening therein adapted to be coaxially related to the axis of the top pole 27 so that a bolt 33 can be utilized to secure the hooks 32 to the top pole 27.

Referring now in more detail to the latching mechanism 24, FIG. 2 illustrates an exploded view thereof. A first member or base unit 36 of the latching mechanism 24 is hollow and includes an internal thread 37 threadedly engaged with the exterior thread 12 at the top end of the bottom pole 11. The base unit 36 includes a pair of diametrically spaced guide slots 38 inclined to the vertical at an angle of about 25O. The guide slots 38 each receive therein an elongated latch pin 39. Each guide slot 38 opens into the passageway 26 through an opening 41. As a result, when the latch pins 39 are received in the guide slots 38, a surface segment of each latch pin 39 will project into the central passageway 26 of the latching mechanism 24 and as illustrated in FIG. 3.

The base unit 36 also has a pair of diametrically spaced and upwardly inclined circumferentially extending slots 42 into which a spherical ball 43 is received in each of the slots 42.

The base unit 36 includes adjacent the upper end thereof an annular groove 44. A shoulder 46 is provided on the base unit 36 and is, in this particular embodiment, oriented between the slots 38, 42 and the lower end of the base unit 36.

A second member 51 of the latching mechanism 24 is comprised of a plurality of parts, namely, a first part 52 and a second part 53. The first part 52 is generally a hollow cylindrical member telescopically receiving therein the base unit 36. The first part has a shoulder 47 on an interior thereof which rests on the shoulder 46. The first part also has a pair of axially aligned and diametrically spaced internally threaded holes 54 therein. The first part 52 also has a pair of diametrically spaced ball capturing slots 56 into which is received a respective one of the balls 43. An annular surface 57 lying in a plane perpendicular to a longitudinal axis A of the central passageway 26 is provided on the upper end of the first part 52.

A first annular flat washer 58 encircles the base unit 36 and rests on the upper surface 57 of the first part 52. Surface segments of the latch pins 39 rest on the upper surface of the annular washer 58. A second annular washer 59, like the annular washer 58, encircles the base unit 36 and rests on surface segments of the two latch pins 39. A compression spring 61 rests at a lower end thereof on the upper surface of the washer 59 and abuts at the other end thereof against a further annular washer 62 encircling the base unit 36 and which rests against a clip ring 63 received in the annular groove 44 of the base unit 36.

The second part 53 of the second member 51 is telescopically received over the previously discussed assembly. The second part 53 has a pair of diametrically spaced and axially aligned holes 64 therein which become axially aligned with the threaded holes 54 in the first part 52. Screws 66 are received in the axially aligned holes 54 and 64 to facilitate securement of the second part 53 to the first part 52. The upper end of the second part 53 has a reduced diameter hole 67 therein in which is secured a lip seal 68. The lip seal 68 fills the space between the internal diameter of the hole 67 and the exterior surface of the top pole 27 as illustrated in FIGS. 3 and 4. A lip 69 on the lip seal 68 slidingly engages the exterior surface of the top pole 27 with sufficient force such as to restrict or throttle the passage of air being displaced from the interior 22 of the bottom pole 11 as the top pole 27 enters therein to assist in reducing the velocity that the top pole 27 will move in a downward direction following a latch release function.

It will be noted that the lower end 29 of the top pole 27 has an enlarged diameter section 71 thereon. It will further be noted that the annular groove 28 is oriented in this enlarged diameter section 71. A tapered surface 72 exists between the enlarged diameter section 71 and the exterior surface of the top pole 27. The interior surface 73 of the base unit 36 includes a tapered shoulder 74 correspondingly shaped to match the tapered section 72 joining the enlarged section 71 to the top pole 27. As a result, the top pole 27 when raised, will not be permitted to move entirely out of its telescoped relation with the bottom pole 11 due to the mutual engagement of the tapered section 72 with the tapered shoulder 74. It will further be noted that when the aforesaid tapered section 72 and tapered shoulder 74 engage one another, the latch pins 39 will enter the locking groove 28.

When it is desired to unlatch the top pole 27 to permit a telescoping movement thereof into the interior 22 of the bottom pole 11, the second part 53 of the latching mechanism 24 is rotated clockwise in direction of the arrows 76 on the second part 53 to cause the balls 43 captured in the ball capturing slots 56 to travel up the ramps defined by the inclined circumferentially extending slots 42 to cause an axial displacement of the second member 51 of the latching mechanism 24 relative to the base unit 36 against the return force of the compression spring 61. That is, the annular washer 58 resting on the upper surface 57 of the first part 52 of the second member 51 is driven upwardly to urge the latch pins 39 upwardly in the angled slots 38. The washer 59 resting on the upper surface of the latch pins 39 is carried therewith and effects a compression of the spring 61 between the aforesaid annular washer 59 and the annular washer 62 abutting the clip ring 63. Once the latch pins have moved simultaneously radially outwardly in the inclined slots 38 a sufficient distance to be effectively removed entirely from the locking grooves 28, the top pole 27 will then be permitted to move axially downwardly into the interior 22 of the bottom pole 11. Air escaping from the interior 22 of the bottom pole 11 will be throttled by the close tolerance spacing between the interior wall surface of the bottom pole 11 and the exterior surface of the enlarged section 71 at the lower end 29 of the top pole 27 and by the lip 69 of the lip seal 68 slidingly engaging the exterior surface of the top pole 27. As a result, the speed at which the top pole 27 drops into the interior of the bottom pole 11 is limited. The elastically yieldable cushion member 23 oriented in the interior of the bottom pole 11 adjacent the lower end thereof cushions the arrival of the lower end 29 of the top pole 27.

A manual release of the attendant's grip urging the second member 51 clockwise to effect a latch release, will cause the spring 61 to urge the latch pins 39 entrapped between the two annular washers 58 and 59 downwardly toward the openings 41 in the base unit 36. This simultaneously causes the balls 43 to be urged down the inclined ramp surface defined by the slots 42 to return the second member 51 in a counter-clockwise direction to its initial position.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A telescoping IV pole, comprising:
   a bottom pole having means at a bottom end thereof for facilitating an orienting of said bottom pole in an upright, vertically oriented position;
   a top pole slidably disposed within said bottom pole in a telescoping manner, said top pole having at a top end thereof support means for facilitating a support of one or more intravenous fluid containers, said top pole having at a bottom end thereof a circumferential locking groove;

a pole latching means for automatically effecting an interlock with said locking groove when said top pole is deployed to an extended position outside of said bottom pole, said pole latching means including plural latch members each being supported for movement into and out of said locking groove, and resilient means for urging said latch members into said locking groove;

manually operable unlocking means for effecting a simultaneous release of said interlock so that said top pole will telescope into said bottom pole; and control means for effecting simultaneous rotational and axial translational movement of said manually operable unlocking means relative to said top and bottom poles so as to effect a simultaneous forceful urging of said latch members out of said locking groove against the urging of said resilient means.

2. The telescoping IV pole according to claim 1, wherein said manually operable unlocking means is secured to a top end of said bottom pole and includes a central passageway therethrough and through which said top pole extends.

3. The telescoping IV pole according to claim 2, wherein said manually operable unlocking means includes latch member guide surfaces opening into and terminating at said passageway and oriented inclined to the vertical, a telescoping of said top pole into said bottom pole, when said latch members are oriented in said locking groove, being prevented by said latch members being clamped between a wall of said locking groove and said guide surfaces.

4. The telescoping IV pole according to claim 3, wherein said control means includes said manually operable unlocking means being comprised of first and second members, said first member being secured to a top end of said bottom pole and having plural inclined ramp surface means thereon and said inclined guide surfaces thereon, said second member having plural socket means each having a roller therein interfacing respective ones of said plural ramp surface means so as to support said second member for rotation relative to said first member and effect said axial translation of said second member in response to a rotational movement of said second member relative to first member caused by said rollers rolling on said ramp surface.

5. The telescoping IV pole according to claim 4, wherein said second member additionally includes a first annular washer encircling said top pole and engaging each said latch member on a side thereof remote from said guide surfaces, said resilient means engaging said annular washer on a side thereof remote from said latch members.

6. The telescoping IV pole according to claim 5, wherein said second member additionally includes a second annular washer engaging each latch member on a side thereof remote from said first annular washer, said second annular washer being supported on said second member for axial translational movement therewith.

7. The telescoping IV pole according to claim 6, wherein said first member includes an abutment for said resilient means, said resilient means comprising a compression spring compressed between said first annular washer and said abutment in response to said axial translational movement of said second member relative to said first member in response to a rotation of said second member in a first direction.

8. The telescoping IV pole according to claim 7, wherein said compression spring, when compressed, has sufficient spring force to continually urge said rollers relative to said ramps and respective said latch members into engagement with an outside surface of said top pole and a corresponding rotational movement of said second member in a second direction opposite said first direction relative to said first member.

9. The telescoping IV pole according to claim 3, wherein said control means includes said manually operable unlocking means being comprised of first and second members, said first member being secured to a top end of said bottom pole, means connecting said first and second members for relative rotational movement and simultaneous relative axial translational movement, said first member having said guide surfaces thereon;

wherein said second member additionally includes a first annular washer encircling said top pole and engaging each said latch member on a side thereof remote from said guide surfaces, said resilient means engaging said annular washer on a side thereof remote from said latch members;

wherein said second member additionally includes a second annular washer engaging each latch member on a side thereof remote from said first annular washer, said second annular washer being supported on said second member for axial translational movement therewith; and wherein said first member includes an abutment for said resilient means, said resilient means comprising a compression spring compressed between said first annular washer and said abutment in response to said axial translational movement of said second member relative to said first member in response to a rotation of said second member in a first direction;

whereby said axial translational movement caused by a rotation of said second member in said first direction relative to said first member effects an axial translational movement of said second washer which in turn imparts an axial translational movement of said latch members relative to said guide surfaces and out of said locking groove and said first washer engaged with said latch members to compress said spring between said abutment and said first washer to release said top pole.

10. The telescoping IV pole according to claim 1, wherein said means at said bottom end of said bottom pole is a tapered fitting adapted to be received in a correspondingly tapered socket.

11. The telescoping IV pole according to claim 10, wherein said tapered fitting includes an exterior facing conical tapered surface.

12. The telescoping IV pole according to claim 11, wherein a transverse hole extends through said tapered fitting.

13. The telescoping IV pole according to claim 1, wherein said manually operable unlocking means includes air throttling means for restricting a displacement of air in said bottom pole when said top pole enters therein.

14. The telescoping IV pole according to claim 13, wherein said throttling means includes an air restricting seal on said second member slidingly engaging an external surface of said top pole.

15. The telescoping IV pole according to claim 1, wherein an elastically yieldable cushion member is provided inside said bottom pole adjacent said bottom end thereof.

* * * * *